United States Patent
Falk

[11] Patent Number: 5,456,702
[45] Date of Patent: Oct. 10, 1995

[54] METHOD FOR LOCALIZED TEMPERATURE REGULATION OF AN OPEN SURGICAL FIELD DURING AN OPERATIVE PROCEDURE

[76] Inventor: Stephen A. Falk, 231 Parrish St., Canandaigua, N.Y. 14424

[21] Appl. No.: 183,067
[22] Filed: Jan. 18, 1994
[51] Int. Cl.⁶ .................................................. A61F 7/12
[52] U.S. Cl. ................................... 607/105; 128/736
[58] Field of Search ........................... 607/96, 104–107, 607/113; 128/736; 604/23

[56] References Cited

U.S. PATENT DOCUMENTS

| | | |
|---|---|---|
| 765,547 | 7/1904 | Brenner. |
| 1,696,440 | 12/1927 | Lubke. |
| 1,904,020 | 4/1933 | Wappler ................................. 607/105 |
| 1,914,026 | 6/1933 | Kirk. |
| 2,093,834 | 9/1937 | Gaugler. |
| 2,110,022 | 3/1938 | Kliesrath. |
| 2,512,559 | 6/1950 | Williams. |
| 2,601,189 | 6/1952 | Wales, Jr.. |
| 2,706,988 | 4/1955 | Weber. |
| 3,418,726 | 12/1968 | Sparks. |
| 3,496,942 | 2/1970 | Shipley ................................. 607/105 |
| 3,691,646 | 9/1972 | Ruffolo. |
| 3,714,947 | 2/1973 | Hardy. |
| 3,757,366 | 9/1973 | Sacher. |
| 3,854,156 | 12/1974 | Williams. |
| 3,881,477 | 5/1975 | Von Otto. |
| 3,908,655 | 9/1975 | Lund. |
| 3,995,620 | 12/1976 | Epley. |
| 4,204,549 | 5/1980 | Paglione. |
| 4,398,535 | 8/1983 | Guibert. |
| 4,572,188 | 2/1986 | Augustine et al.. |
| 4,660,388 | 4/1987 | Greene, Jr.. |
| 4,745,922 | 5/1988 | Taylor. |
| 4,779,593 | 10/1988 | Kieman. |
| 4,817,635 | 4/1989 | Joines et al.. |
| 4,844,074 | 7/1989 | Kurucz ................................. 607/105 |
| 4,955,377 | 9/1990 | Lennox et al. ....................... 607/105 |
| 4,969,459 | 11/1990 | Gusakov. |
| 5,042,469 | 8/1991 | Augustine. |
| 5,054,723 | 10/1991 | Arnold. |
| 5,106,373 | 4/1992 | Augustine et al.. |
| 5,184,612 | 2/1993 | Augustine. |
| 5,203,320 | 4/1993 | Augustine. |
| 5,224,492 | 7/1993 | Takahashi et al.. |

FOREIGN PATENT DOCUMENTS 3331299  3/1985  Germany.

OTHER PUBLICATIONS

Thyroid Disease, Endocrinology, Surgery, Nuclear Medicine, and Radiotherapy, Stephen A. Falk, M.D., F.A.C.S, Raven Press, NY.

*Primary Examiner*—Angela D. Sykes
*Attorney, Agent, or Firm*—Cumpston & Shaw

[57] ABSTRACT

A heating unit and control system for warming tissue exposed during an open surgical procedure to an ambient temperature below body temperature, such that the exposed tissue remains substantially at body temperature. Heated air is blown through a duct to be introduced into the surgical field where the temperature of the tissue and the temperature of the exiting air is monitored and processed by a control system to insure maintenance of the tissue at substantially body temperature.

15 Claims, 2 Drawing Sheets

METHOD FOR LOCALIZED TEMPERATURE REGULATION OF AN OPEN SURGICAL FIELD DURING AN OPERATIVE PROCEDURE

FIELD OF THE INVENTION

The present invention relates to a method and apparatus for reducing surgery induced trauma, and more particularly, to a method and apparatus for locally controlling the temperature of an exposed body cavity during an open surgical procedure to reduce post operative complications. During current surgical procedures, organs are exposed to an ambient temperature below body temperature, which cools the organs and may produce pathological changes in the organ. The present invention includes a method and apparatus for maintaining the exposed organs at substantially body temperature to reduce post operative complications and pathological effects.

BACKGROUND OF THE INVENTION

A particular application of the present invention is directed to reducing post-operative trauma following surgery of the parathyroid glands, thyroid gland or adjacent structures in the neck. Calcium homeostasis (i.e. the maintenance of a normal level of calcium in the serum component of the blood) is an important requirement of living organisms. Normal calcium levels are necessary for coagulation of blood, normal bone development, proper function of the nervous, muscular, cardiovascular and endocrine systems and for many cellular processes fundamental to normal function of all cells in the human body.

Calcium homeostasis is controlled through complex and dynamic interactions of bone in the skeleton (serving as a reservoir of calcium), intestines (where dietary Calcium is absorbed into the blood), the kidneys (which secrete 1,25 dihydroxyvitamin D causing calcium absorption in intestines and which excretes calcium into urine in varying amounts), parathyroid hormone (secreted by the parathyroid glands in the neck), and the serum component of blood (serving as transport medium among these organs). Through complex and dynamic interactions of these organs, the human body continually tries to maintain a normal level of serum calcium (8.5–11 mg/100 ml serum).

Parathyroid hormone maintains normal levels of serum calcium by means of two effects. It mobilizes calcium from bone into serum and inhibits excretion of calcium from kidneys into urine. If there is an insufficient amount of parathyroid hormone (hypoparathyroidism), the level of serum calcium decreases (hypocalcemia). Hypocalcemia can be mild and asymoptomatic or severe and life threatening producing paresthesias, tetany, carpopedal spasm, laryngospasm, convulsions, cardiac arrhythmias and death.

It is known that after surgery of the parathyroid glands, thyroid gland or adjacent structures in the neck, hypocalcemia can occur. Hypocalcemia is classified as temporary or permanent. Ischemia (decrease in oxygen supplied due to impairment of blood flow) of the parathyroid glands is the most commonly accepted cause of temporary hypoparathyroidism. Ischemia may also arise from temporary vascular spasm of the parathyroid blood vessels which results from surgical trauma or permanent impairment of blood flow through the parathyroid vessels owing to surgical trauma, with parathyroid function returning as neovascularization is established after surgery.

The appearance of hypocalcemia or its symptoms requires the patient to remain in the hospital until the hypocalcemia or its symptoms are addressed. The lengthened hospital stay increases costs and reduces the efficiency of the hospital and the attending physicians. Therefore, there is a need to safely reduce hypocalcemia induced during surgical procedures involving the parathyroid glands, the thyroid gland or adjacent structures in the neck. In addition, the general need exists for reducing surgery induced trauma on tissues exposed during open surgery.

SUMMARY OF THE INVENTION

The present invention includes the recognition of post-operative complications by thermally induced trauma to organs exposed in an open surgical field during a surgical procedure. The present invention includes a method and apparatus for maintaining the temperature of exposed organs and glands at substantially body temperature in an open surgical field during the operative procedure wherein an ambient temperature conducive to surgeons is maintained. In a preferred embodiment of the present invention, the temperature of at least a portion of an open surgical field is maintained above a reduced ambient temperature and substantially at body temperature.

During most surgical procedures, the operating room or ambient temperature is substantially below body temperature. Although more than ten degrees below body temperature, an operating room temperature of 85° induces accelerated fatigue in surgeons and operating staff. Such a temperature also induces significant perspiration which may contaminate the surgical fields as well as lead to fatigue in surgeons and possible errors in technique and inhibit control over the surgical instruments. Therefore, as the surgeon is wearing a surgical gown, gloves, hat, mask and goggles, the operating room temperature is often maintained at approximately 68° to 72° F.

It is known by the inventor that exposure of certain organs, even though in contact with the open body cavity, to such reduced temperature will induce hypothermia. It is further known that hypothermia of the parathyroid glands may cause temporary hypoparathyroidism and temporary hypocalcemia. Hypothermia of the parathyroid glands or thyroid gland and adjacent structures results from the cooling of the parathyroid glands after their exposure during an open surgical procedure in an operating room with an ambient temperature lower than body temperature.

In a preferred embodiment of the present invention, a flow generation unit is selectively controlled to produce an air flow of a predetermined rate at a given temperature. The air flow passes through a duct and is locally introduced into a portion of an exposed body cavity during an open surgical procedure. The flow generation unit includes a heater for heating the air flow and a blower for generating the flow, and may include a filter/sterilizer and a humidifier for conditioning the air to be introduced into the surgical field.

A control system monitors the temperature of the fluid exiting the duct as well as the temperature of the gland or adjacent tissue and compares the temperatures to a preset or predetermined temperature to regulate the flow generation unit to maintain the organ at substantially the desired temperature.

DETAILED DESCRIPTION OF THE PREFERRED EMBODIMENTS

Although the present invention may be used for either selectively maintaining a portion of an open surgical field below, at, or the above body temperature, the present invention is described in terms of maintaining a specific gland or area of the surgical field substantially at body temperature. The alternative temperatures can be readily achieved through the present invention.

Figure 1:
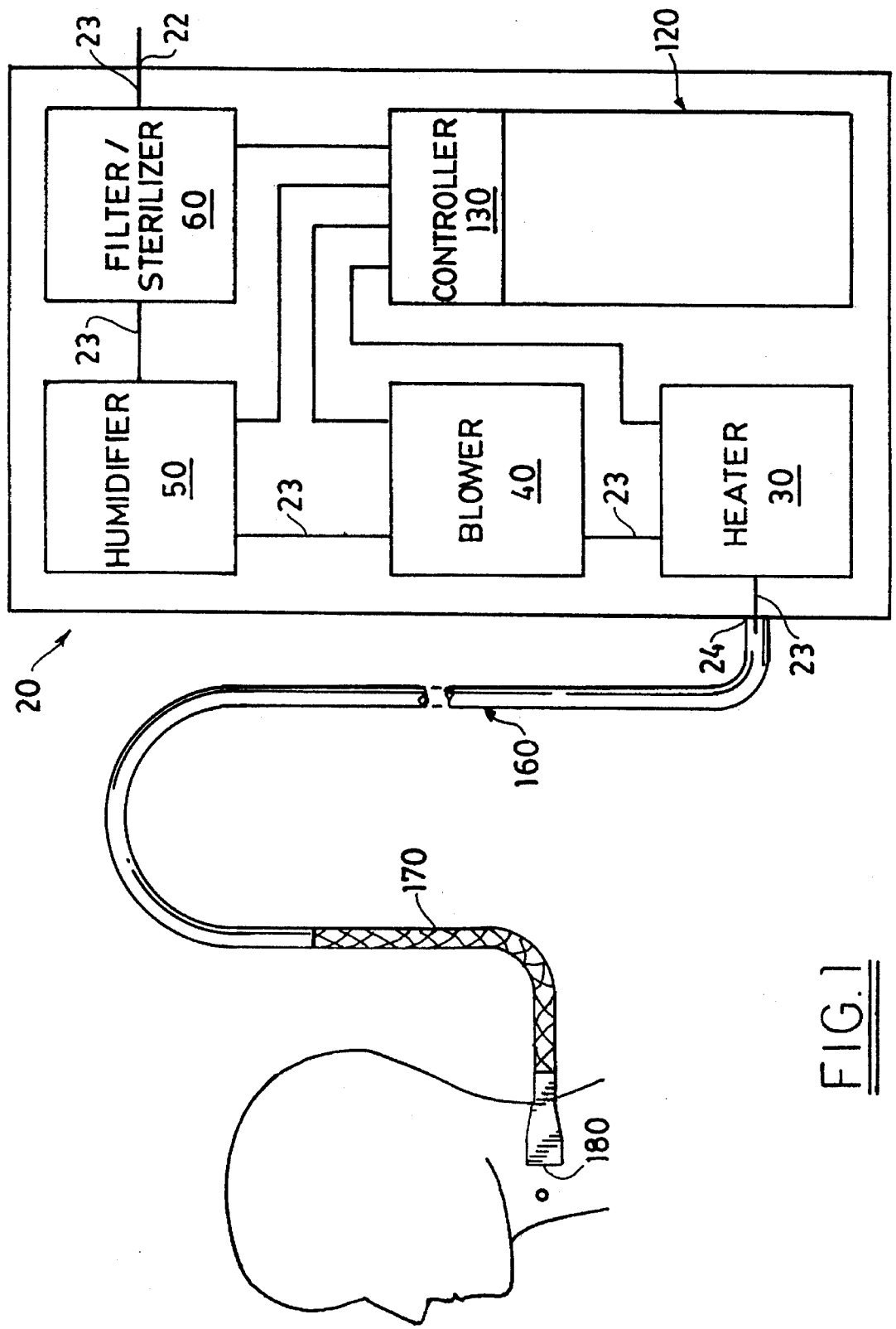
FIG. 1 is a schematic view of the components of the flow generator and field of use.

Referring to FIG. 1, the present invention includes a flow generation unit 20 operatively connected to a control system 120 for creating a controlled air flow through a duct 160 to be locally introduced into a portion of a surgical field.

The surgical field includes an open body cavity which exposes a potion of the patient's interior. The exposed area of the surgical field may be relatively small, directly exposing few if any temperature sensitive organs, or the area may be relatively large exposing a number of organs, some of which exhibit sensitivity to the thermal stress of open surgery. By maintaining the relevant tissues at body temperature, temporary disfunction of the tissue is reduced. That is, abnormal physiology resulting from thermal stress is precluded. In view of the ready applicability of the present invention to any size surgical field, the description is directed to the application of the invention to a surgical field that exposes one of the thyroid or parathyroid glands, or adjacent tissue to the temperature of an ambient operating environment which is below body temperature. The "adjacent tissue" includes that tissue which, when exposed to the ambient temperature adversely effects the temperature of the temperature sensitive gland. Therefore, the adjacent tissue is partially determined by the temperature of the operating environment, the length of the surgery and the insulating characteristics of the tissue and the temperature sensitivity of the relevant gland.

Flow Generation Unit

The air flow generation unit 20 includes a heater 30, a blower 40, a humidifier 50 and a filter/sterilizer 60. Although described as separate components of a single unit, each of the heater 30, blower 40, humidifier 50 and filter/sterilizer 60 may be a separate module operatively interconnected, or housed within a single unit. As shown in FIG. 1, the air flow generation unit 20 includes an air inlet 22 and an air outlet 24, wherein the heater 30, the blower 40, the humidifier 50 and the filter/sterilizer 60 are functionally intermediate of the inlet and the outlet. As shown in FIG. 1, a flow path 23 connects the individual components and the inlet 22 to the outlet 24.

The filter/sterilizer 60 may be one known in the art such as a "MICROCON" with high efficiency filter manufactured by Biological Controls. The filter/sterilizer 60 may include only a filter for filtering foreign matter of a size down to 0.3 microns from the air. Alternatively, the filter/sterilizer 60 may be limited to a sterilizer as well known in the industry such as an autoclave type device. The filter/sterilizer 60 may also employ both technologies as dictated by operating conditions. Preferably, the filter/sterilizer 60 is remotely controllable so that either or both the filtering and sterilization capabilities may be selectively used.

The humidifier 50 introduces water vapor into the air flow and may be any of commercially available units such as Nebutherm I nebulizer heater manufactured by Automatric Liquid Packagings, Health Care Products Division. Preferably, the humidifier 50 is remotely controllable so that humidification of the air flow may be manually adjusted or automatically controlled to achieve a predetermined humidity or vapor content.

The blower 40 is a controllable fan or impeller driven unit for generating an air flow. The blower 40 may be any of a variety of controllable flow generators which has a variable flow rate and may be remotely controlled.

The specific heater 30 is a matter of design choice and may be selected from those known in the art such as Nebutherm I nebulizer manufactured by Automatric Liquid Packagings, Health Care Products Division. Although the heater 30 is preferably an ohmic or resistance heater, the heater may employ a fluid bath of a controlled temperature through which an air flow duct passes so that the temperature of the air is regulated by the temperature of the fluid bath.

While the flow path 23 through the flow generation unit 20 is shown as passing from the inlet 22 through the filter/sterilizer 60, the humidifier 50, the blower 40 and the heater 30, to exit through the outlet 24, the components may be arranged in any order as dictated by design considerations. That is, the flow path through the components is dictated by the need to accurately regulate the temperature of the air flow, as well as maintain the necessary humidity and purity.

Duct

The duct 160 is fluidly connected to the outlet 24 of the flow generation unit 20 and extends to the surgical field. The duct 160 terminates at a discharge port 180 for locally introducing the fluid flow into the surgical field. The duct 160 is flexible and has a sufficient length to extend between the flow generation unit 20 and the surgical field. Preferably, the portion of the duct 160 which may contact the patient, the patient portion 170, is insulated so that this portion of the duct is substantially at ambient temperature. The patient portion 170 has a typical length of approximately three feet. The insulation on the duct 160 may be an exterior layer or integrally formed with the patient portion of the duct. Preferably, the insulation is non reactive to humans and is disposable or sterilizable.

Figure 2:
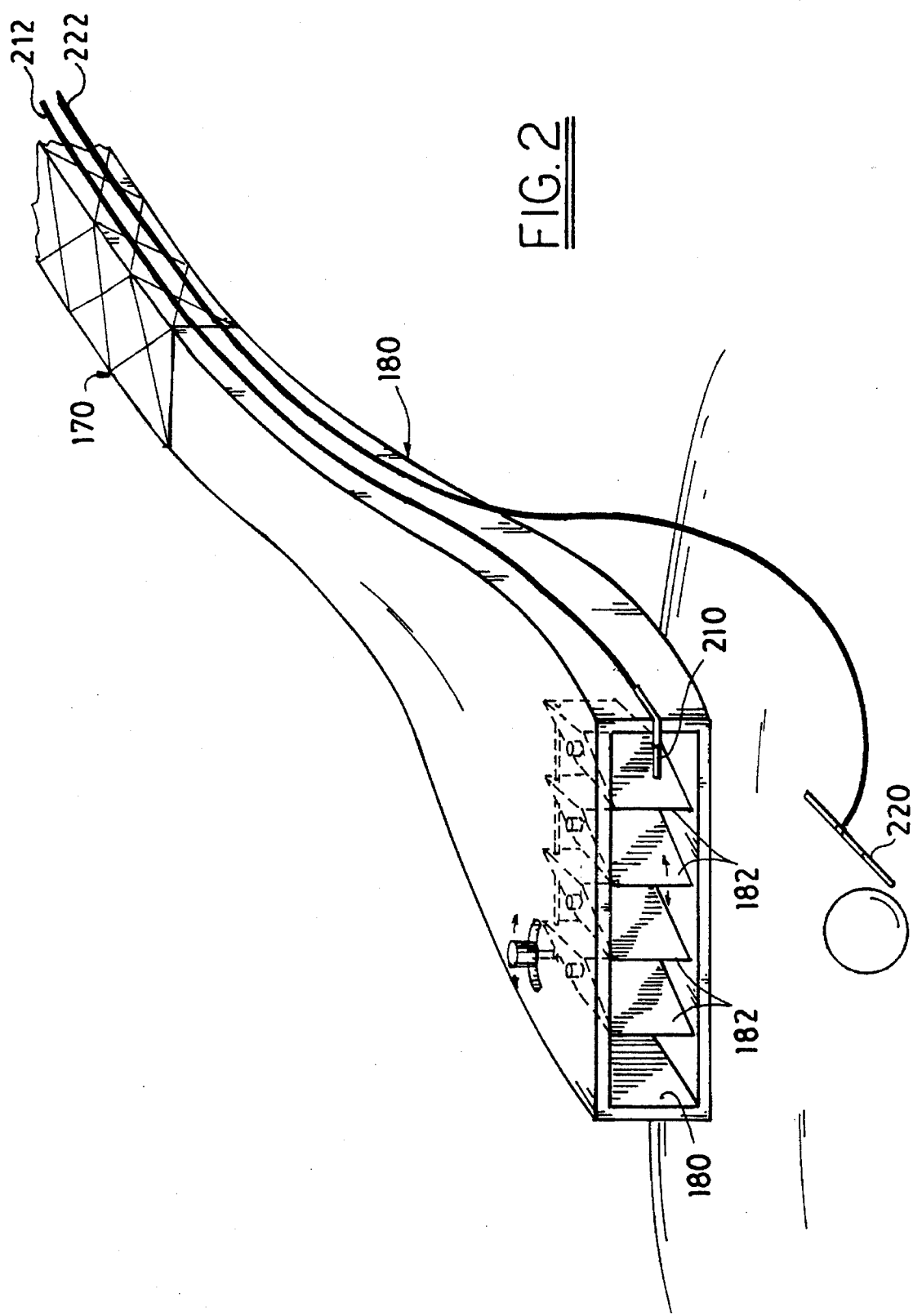
FIG. 2 is a perspective view of the duct for discharging the air flow at or adjacent the relevant gland.

Referring to FIG. 2 in a preferred embodiment, the discharge port 180 is selectively separable from the patient portion 170 and the remaining length of the duct 160, and is sterilizable or disposable. The discharge port 180 defines an opening for locally directing the fluid flow over a specific local region. The cross section of the discharge port 180 is such that the air flow is substantially uniform across the area. In addition, the discharge port 180 also includes a directional vane assembly 182 for selectively dispersing the air flow over an area of the surgical field having width less than, equal to or substantially greater than the width of the discharge port. The discharge port 180 is preferably formed of a plastic resin and is disposable or sterilizable. The mechanical connection of the discharge port 180 to the patient portion 170 includes contacts for the temperature sensors, as discussed infra.

In addition, the patient portion 170 and the discharge port 180 have a non circular cross section. The cross section of these components is substantially rectangular, so that one of the longer sides contacts the patient and the shorter end walls are approximately one to two inches high. Alternatively, the patient portion 170 may be any shape that is unobstrusive and reduces interference with the areas adjacent the surgical field. The patient portion 170 is fixable relative to the surgical field so that the discharge port may be located at the desired location adjacent the body cavity to substantially preclude unintended dislocation.

Temperature Sensors

The present invention employs a fluid temperature sensor 210 and a tissue temperature sensor 220. The temperature sensors 210,220 are operably connected to control system 120 by lines 212,222, respectively. The fluid temperature sensor 210 is located at the discharge port 180 to measure the temperature of the fluid flow passing through the discharge port. Although the fluid temperature sensor 210 is shown at the discharge port 180, the sensor may be located at other positions, wherein the fluid temperature exiting the discharge port is calculated rather than directly measured.

The tissue temperature sensor 220 is positioned in or adjacent the tissue to be maintained at a predetermined temperature. The tissue temperature sensor 220 is a needle tip or contact tip and includes a disposable or sterilizable wire or conductor. The flow temperature sensor and tissue temperature sensor lines 212,222 may be separate from or bound to, or integral with the duct and mechanically connectable to the sensor and attached wire. That is, the lines 212,222 extending from the sensors to the control system 120 may be attached to the duct 160, or may be separate. Preferably, the fluid temperature and tissue temperature lines 212,222 are integrally connected to the duct 160 so that the fluid and tissue temperature sensors may be disposed and replaced with sterile pieces.

Control System

The control system 120 is operably connected to the flow generation unit 20, the fluid and tissue temperature sensors 210, 220 and the patient. The control system 120 may be a modular unit or integrally connected to the flow generation unit 20. The control system 120 includes a controller 130 for receiving (monitoring) signals and comparing the signals and generating control signals. The controller 130 may be a desktop computer or a dedicated integrated chip and accompanying circuitry. The controller 130 includes an input mechanism for setting a predetermined temperature to be maintained in the surgical field, as well as a sensor for measuring the ambient operating room temperature. Within the flow generation unit 20, the controller 130 is operatively connected to the heater 30 and the blower 40 and may be connected to the humidifier 50 and filter/sterilizer 60.

The controller 130 compares the fluid temperature and the tissue temperature with the preset or predetermined temperature and regulates the amount of heat generated by the heater 30 and air flow rate generated by the blower 40. The controller 130 also regulates the air flow path to by-pass either the humidifier 50 or the filter/sterilizer 60 or both as dictated by surgeon recommendations.

Procedure

As previously stated, although the present use is described in terms of maintaining parathyroid glands at substantially body temperature to reduce post operative hypocalcemia by locally introducing a heated airflow into a surgical field, the present invention may be applied to any organ or gland which may exhibit post operative dysfunction as a result of thermal stress or hypothermia induced during surgical procedures. That is, the cooling of body portions exposed during surgery may result in abnormal physiology of cooled tissue. The abnormal physiology is determined by the specific tissue that is cooled such that abnormal physiology produces changes that will cause pathological or negative effects on a patient.

The patient is draped and the sterile patient portion of the duct is affixed relative to the surgical field. The discharge port 180 is located adjacent or at the exposed body cavity to introduce the fluid flow into the surgical field and into the exposed body cavity.

During normal operation, air is drawn in through the inlet 22 of the flow generation unit 20 and passes through the filter/sterilizer 60 and humidifier 50. The air is then drawn in to and discharged from the blower 40 and passes through the heater 30 to exit the flow generation unit 20 at a given temperature. The air passes through the duct 160 to be discharged at the discharge port 180. The temperature of the flow exiting the discharge port 180 is measured by the fluid temperature sensor 210 and the signal is sent to the control system 120 via line 212. The tissue temperature sensor 220 provides the temperature of the relevant tissue to the control system 120 via line 222. By comparing the flow temperature and the tissue temperature, the control system 120 selectively adjusts the blower 40 and heater 30 as necessary so that the flow temperature is increased or decreased to maintain the tissue temperature at the predetermined temperature (substantially body temperature in the present embodiment). Preferably, the humidifier 50 is set to introduce sufficient water vapor into the air flow to preclude desiccation of the exposed tissue.

To prevent patient burn, the temperature of the flow exiting the discharge port 180 should not be higher than a certain temperature above which the patient's skin or internal organs may be burned or damaged (burn threshold). The burn threshold depends upon the flow rate, the flow temperature, and the humidity of the air flow, as well as the operating room temperature. The fluid temperature sensor 210 measures the temperature of the flow exiting the duct and upon the controller 130 receiving a fluid temperature greater than the burn threshold may generate an alert to the staff through audio or video alarms as well as automatically reduce the temperature of the air flow, unless manually overridden.

By locating the discharge port 180 adjacent the exposed tissue, the air flow is not substantially occluded or interfered with by the surgeon or surgical instruments. In addition, the local introduction of the air flow and its relatively low volume compared to the volume of the operating room prevents heating of the operating room.

In an alternative embodiment, the thermal energy may be locally introduced by a non ionizing radiative energy source such as infra radiation, microwave or laser. The use of the non ionizing radiative energy is controlled in the same manner as with the air flow. That is, the temperature of the relevant tissue is monitored and the amount of energy introduced into the area is controlled as necessary to maintain the desired temperature.

While a preferred embodiment of the invention has been shown and described with particularity, it will be appreciated that various changes and modifications may suggest themselves to one having ordinary skill in the art upon being apprised of the present invention. It is intended to encompass all such changes and modifications as fall within the scope and spirit of the appended claims.

What is claimed is:

1. A method for reducing temporary hypocalcemia after a surgical procedure which exposes one of a parathyroid gland and adjacent tissue to a temperature less than body temperature, comprising:

(a) generating a fluid flow;

(b) contacting the fluid flow on at least a portion of one of the exposed parathyroid gland and the adjacent tissue;

(c) measuring the temperature of one of the parathyroid gland and the adjacent tissue; and (d) regulating the temperature of the fluid flow in response to the measured temperature to maintain the temperature of one of the parathyroid gland and the adjacent tissue substantially at body temperature.

2. The method of claim 1, further comprising sufficiently humidifying the fluid to substantially preclude desiccating of one of the parathyroid gland and the adjacent tissue.

3. The method of claim 1, wherein the temperature of the fluid flow is greater than body temperature.

4. The method of claim 1, wherein the temperature of the fluid flow is below a burn threshold.

5. The method of claim 1, wherein the fluid flow comprises air.

6. The method of claim 1, further comprising sterilizing a quantity of the fluid prior to exposure to one of the parathyroid gland and the adjacent tissue.

7. A method for reducing temporary hypocalcemia after a surgical procedure which exposes one of a parathyroid gland and adjacent tissue to an ambient temperature less than body temperature for a given period of time, comprising:

(a) monitoring the temperature of one of the parathyroid gland and adjacent tissue during at least a portion of the given period of time;

(b) contacting a fluid flow with at least a portion of one of the exposed parathyroid gland and the adjacent tissue the fluid having a sufficient temperature to maintain the parathyroid gland at a desired temperature to preclude temporary disfunction of the parathyroid gland; and (c) regulating the temperature of the fluid flow in response to the temperature of one of the parathyroid gland and adjacent tissue.

8. The method of claim 7, further comprising sufficiently humidifying the fluid to substantially preclude desiccating of one of the parathyroid gland and the adjacent tissue.

9. The method of claim 7, further comprising heating the fluid prior to exposure to one of the parathyroid gland and the adjacent tissue.

10. The method of claim 7, wherein the fluid substantially comprises air.

11. The method of claim 7, further comprising sterilizing a quantity of the fluid prior to exposure to one of the parathyroid gland and the adjacent tissue.

12. The method of claim 7, further comprising filtering the fluid to remove a portion of any biological impurities in the fluid prior to contact with one of the parathyroid gland and the adjacent tissue.

13. The method claim 7, wherein the desired temperature is substantially equal to body temperature.

14. The method of claim 7, wherein the temperature of the fluid flow is greater than body temperature.

15. The method of claim 7, wherein the temperature of the fluid flow is less than a burn threshold.

* * * * *